United States Patent [19]

Shuman

[11] 4,283,330
[45] Aug. 11, 1981

[54] PHARMACOLOGICALLY ACTIVE PEPTIDES

[75] Inventor: Robert T. Shuman, Greenwood, Ind.

[73] Assignee: Eli Lilly and Company, Indianapolis, Ind.

[21] Appl. No.: 104,349

[22] Filed: Dec. 17, 1979

[51] Int. Cl.$^3$ ..................... C07C 103/52; A61K 37/00
[52] U.S. Cl. ............................. 260/112.5 R; 424/177
[58] Field of Search ................................ 260/112.5 R

[56] References Cited

FOREIGN PATENT DOCUMENTS

| | | | |
|---|---|---|---|
| 870819 | 3/1979 | Belgium | 260/112.5 R |
| 2741393 | 3/1978 | Fed. Rep. of Germany | 260/112.5 R |
| 774479 | 7/1977 | South Africa | 260/112.5 R |

OTHER PUBLICATIONS

McGregor et al., Life Science 23, 1371–1378 (1978).

*Primary Examiner*—Delbert R. Phillips
*Attorney, Agent, or Firm*—William C. Martens, Jr.; Arthur R. Whale

[57] ABSTRACT

Compounds of the formula

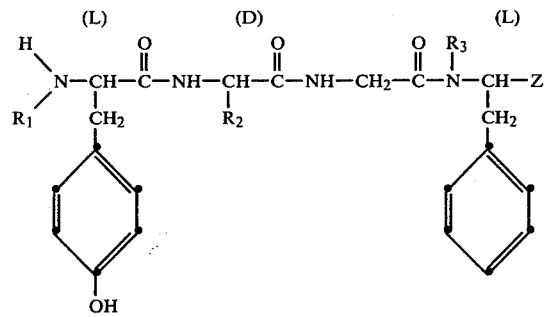

and pharmaceutically acceptable non-toxic acid addition salts thereof, in which L and D define the chirality;

$R_1$ is hydrogen or $C_1$–$C_3$ primary alkyl;

$R_2$ is $C_1$–$C_4$ primary or secondary alkyl, allyl, cyclopropylmethyl, $C_1$–$C_2$ hydroxyalkyl, or —(CH$_2$)$_m$—U—CH$_3$ in which U is —S— or >S—O and m is 1 or 2;

$R_3$ is cyclopropylmethyl or allyl; and

Z is —CH$_2$OR$_4$,

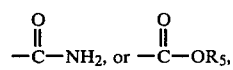

in which $R_4$ is hydrogen, acetyl, or acetoxymethyl and $R_5$ is $C_1$–$C_3$ alkyl; are useful analgesic agents.

13 Claims, No Drawings

PHARMACOLOGICALLY ACTIVE PEPTIDES

BACKGROUND OF THE INVENTION

This invention relates to a novel class of compounds which exhibit analgesic activity.

Recently, endogenous substances having morphine-like properties have been extracted from mammalian brain or csf. These substances, named enkephalin, have been identified by Hughes et al., *Nature*, 258, 577 (1975) as pentapeptides having the following sequences:

H-Tyr-Gly-Gly-Phe-Met-OH

H-Tyr-Gly-Gly-Phe-Leu-OH.

These compounds are referred to as methionine-enkephalin and leucine-enkephalin, respectively.

Although methionine and leucine enkephalin have been shown to exhibit analgesic activity in mice upon administration intracerebroventricularly [Buscher et al., *Nature*, 261, 423 (1976)], they are practically devoid of any useful analgesic activity when administered parenterally.

Therefore, since the discovery of the enkephalins, much effort has been devoted to preparing analogs of the enkephalins in the hope of finding compounds having enhanced activity and practical utility due to their bioavailability by parenteral or oral administration.

Dutta et al., *Life Sciences* 21, pp. 559–562 (1977) report certain structure modifications which, they suggest, tend to enhance potency. They suggest activity can be enhanced by any or all of the following:

(a) substitution of Gly in position 2 by certain D- or α-aza-amino acids;

(b) conversion of the terminal carboxyl to the methyl ester or the amide;

(c) modification of the Phe in the 4-position by α-aza substitution, N-methylation, or hydrogenation of the aromatic ring.

In addition, Roemer et al., *Nature* 268, pp. 547–549 (1977), suggest modification of the Met[5] to its corresponding carbinol and oxidation of the Met sulfur to the sulfoxide as useful modifications.

Another structural modification of significance is that reported in Belgian Pat. No. 859,026. This publication suggests enhancement of activity and bioavailability of enkephalin analogs by insertion of a D-amino acid residue in position 2, conversion of the terminal carboxyl to an amide, and N-alkylation of the amino acid residue in position 5.

A class of analogs of enkephalin having a high level of analgesic activity has now been discovered. The compounds of this invention are tetrapeptides having the residue of the L-phenylalanine in the 4-position of the peptide substituted at its nitrogen by cyclopropylmethyl or allyl.

SUMMARY OF THE INVENTION

Thus, this invention relates to a class of compounds having the formula

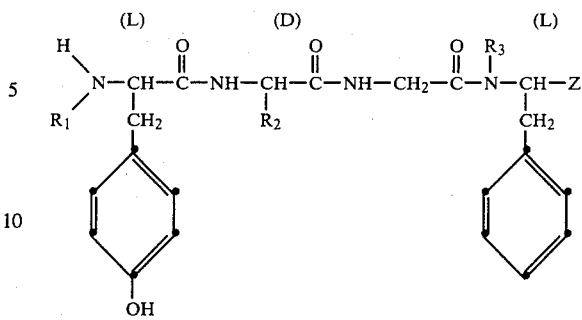

and pharmaceutically acceptable non-toxic acid addition salts thereof, in which L and D define the chirality;

$R_1$ is hydrogen or $C_1$–$C_3$ primary alkyl;

$R_2$ is $C_1$–$C_4$ primary or secondary alkyl, allyl, cyclopropylmethyl, $C_1$–$C_2$ hydroxyalkyl, or —(CH$_2$)$_m$—U—CH$_3$ in which U is —S— or >S—O and m is 1 or 2;

$R_3$ is cyclopropylmethyl or allyl; and

Z is —CH$_2$OR$_4$,

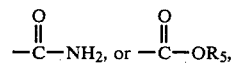

in which $R_4$ is hydrogen, acetyl, or acetoxymethyl and $R_5$ is $C_1$–$C_3$ alkyl.

DETAILED DESCRIPTION OF THE INVENTION

As indicated above, the compounds of this invention have the following structure:

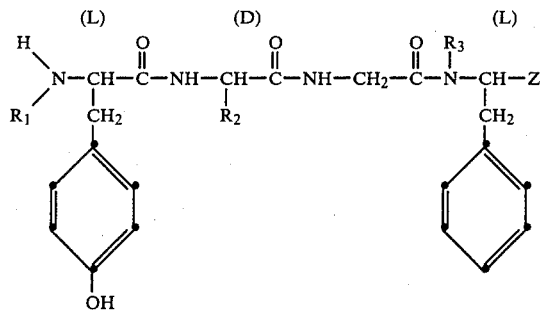

Also included are the pharmaceutically acceptable non-toxic acid addition salts of these compounds.

Pharmaceutically acceptable non-toxic acid addition salts include the organic and inorganic acid addition salts, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. Preferably, the acid addition salts are those prepared from hydrochloric acid, acetic acid, or succinic acid. Any of the above salts are prepared by conventional methods.

As will be noted from the definition of the various substituents which appear in the above structure, the compounds which are defined by this structure are tetrapeptides, the C-terminal portion of which is a primary alcohol or its ester derivative, a primary amide, or a lower alkyl ester.

The stereoconfiguration of the compounds of this invention is an essential feature thereof. For the sake of convenience, the amino acid residues of the tetrapeptides of this invention are numbered sequentially beginning with the residue at the terminal amino function. The chirality of the amino acid residues, reading from Position 1 through Position 4, is L, D, none, and L. The residue in Position 3 is a glycine moiety, and, thus, no chirality as to this residue exists.

The group $R_1$ as used herein is defined to include the group "$C_1$–$C_3$ primary alkyl." By the term "$C_1$–$C_3$ primary alkyl" is meant methyl, ethyl, and n-propyl.

The group $R_5$ as used herein is defined to include the group "$C_1$–$C_3$ alkyl". By the term "$C_1$–$C_3$ alkyl" is intended methyl, ethyl, n-propyl and isopropyl.

The group $R_2$ appearing in the above structural formula is defined to include the group "$C_1$–$C_4$ primary or secondary alkyl". By the term "$C_1$–$C_4$ primary or secondary alkyl" is meant methyl, ethyl, n-propyl, isopropyl, n-butyl, isobutyl, and sec-butyl.

The group $R_2$ is also defined as "$C_1$–$C_2$ hydroxyalkyl". By the term "$C_1$–$C_2$ hydroxyalkyl" is meant hydroxymethyl, 1-hydroxyethyl, and 2-hydroxyethyl.

The group $R_2$ appearing in the above structural formula also is defined to include the group —(CH$_2$)$_m$—U—CH$_3$ in which U is —S— or S—O and m is 1 or 2. By the term "—(CH$_2$)$_m$—U—CH$_3$" is meant methylthiomethyl, methylthioethyl, methylsulfinylmethyl, and methylsulfinylethyl.

With respect to the particular position residues of the tetrapeptides of this invention, the following considerations prevail:

(A) Position 1

This position represents the amino-terminal portion of the peptide. The residue is that which results from L-tyrosine. The residue can be N-unsubstituted, in which case $R_1$ is hydrogen. Moreover, the residue can be substituted by a $C_1$–$C_3$ primary alkyl, giving rise to N-methyl, N-ethyl-, or N-n-propyl-. For compounds having exceptionally high levels of analgesic activity when administered parenterally, the tyrosyl residue which is present in Position 1 preferably is N-unsubstituted. For compounds having exceptionally high levels of analgesic activity when administered orally, the tyrosyl residue which is present in Position 1 preferably is N-substituted. In the event that the tyrosyl is N-substituted, the N-substituent preferably is methyl.

(B) Position 2

The amino acid residue which is present in the second position of the peptides of this invention must be the D stereoisomer and is any of several amino acid residues. These include residues derived from D-alanine (Ala) ($R_2$ is methyl), D-α-aminobutyric acid (Abu) ($R_2$ is ethyl), D-norvaline (Nva) ($R_2$ is n-propyl), D-valine (Val) ($R_2$ is isopropyl), D-norleucine (Nle) ($R_2$ is n-butyl), D-leucine (Leu) ($R_2$ is isobutyl), D-isoleucine (Ile) ($R_2$ is sec-butyl), D-allylglycine [Gly(Al)] ($R_2$ is allyl), D-cyclopropylmethylglycine [Gly(Cp)] ($R_2$ is cyclopropylmethyl), D-methionine (Met) ($R_2$ is 2-methylthioethyl), D-(S-methyl)cysteine [Cys(Me)] ($R_2$ is methylthiomethyl), D-methionine sulfoxide [Met(O)] ($R_2$ is methylsulfinylethyl), D-(S-methyl)cysteine sulfoxide [Cys(Me)(O)] ($R_2$ is methylsulfinylmethyl), D-serine (Ser) ($R_2$ is hydroxymethyl), D-threonine (Thr) ($R_2$ is 1-hydroxyethyl), and D-homoserine (Hse) $R_2$ is 2-hydroxyethyl). Preferably, $R_2$ is $C_1$–$C_4$ primary or secondary alkyl or $C_1$–$C_2$ hydroxyalkyl. of the two groups, $C_1$–$C_4$ primary or secondary alkyl is more preferred, and of the latter, the residue derived from D-alanine.

(C) Position 3

The amino acid residue present in this position is that derived from glycine (Gly).

(D) Position 4

The amino acid residue present in this position is that derived from L-phenylalanine (Phe). The residue is substituted ($R_3$) at its amino nitrogen by cyclopropylmethyl or allyl.

The residue present in the C-terminal position of the compounds of this invention is an amino acid structurally derivatized to its amide (Z is

its primary alcohol or ester derivative (Z is —CH$_2$OR$_4$), or its $C_1$–$C_3$ alkyl ester (Z is

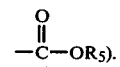

Preferably, the residue is derivatized to its primary amide, its alcohol, or its ester derivative. Of the above, the primary amide is most preferred.

In this specification, the following abbreviations, most of which are well known and are commonly used in the art, are employed:

Abu—α-aminobutyric acid
Ala—alanine
Cys—cysteine
Cys(Me)—(S-methyl)cysteine
Cys(Me)(O)—(S-methyl)cysteine sulfoxide
Gly—glycine
Gly(Al)—allylglycine
Gly(Cp)—cyclopropylmethylglycine
Hse—homoserine
Ile—isoleucine
Leu—leucine
Met—methionine
Met(O)—methionine sulfoxide
Nle—norleucine
Nva—norvaline
Phe—phenylalanine
Ser—serine
Thr—threonine
Tyr—tyrosine
Val—valine
Ac—acetyl
AcOMe—acetoxymethyl
Al—allyl
Cp—cyclopropylmethyl
Me—methyl
Et—ethyl
Ip—isopropyl
Pr—n-propyl
Bu—n-butyl
i-Bu—isobutyl
t-Bu—t-butyl
s-Bu—sec-butyl
Boc—t-butyloxycarbonyl
Bzl—benzyl
Cbz—benzyloxycarbonyl DCC—N,N'-dicyclohexylcarbodiimide
HBT—1-hydroxybenzotriazole
DMF—N,N-dimethylformamide
TFA—trifluoroacetic acid
THF—tetrahydrofuran
DEAE—diethylaminoethyl
IBCF—isobutyl chloroformate
18-crown-6—1,4,7,10,13,16-hexaoxacyclooctadecane Examples of typical compounds of this invention include the following, any or all of which may be in the form of a pharmaceutically acceptable nontoxic acid addition salts:

H-L-Tyr-D-Ala-Gly-L-(N-Cp)Phe-NH$_2$;
H-L-Tyr-D-Ala-Gly-L-(N-Al)Phe-NH$_2$;
H-L-Tyr-D-Abu-Gly-L-(N-Cp)Phe-NH$_2$;
H-L-Tyr-D-Abu-Gly-L-(N-Al)Phe-NH$_2$;
H-L-Tyr-D-Nva-Gly-L-(N-Cp)Phe-NH$_2$;
H-L-Tyr-D-Nva-Gly-L-(N-Al)Phe-NH$_2$;
H-L-Tyr-D-Val-Gly-L-(N-Cp)Phe-NH$_2$;
H-L-Tyr-D-Val-Gly-L-(N-Al)Phe-NH$_2$;
H-L-Tyr-D-Nle-Gly-L-(N-Cp)Phe-NH$_2$;
H-L-Tyr-D-Nle-Gly-L-(N-Al)Phe-NH$_2$;
H-L-Tyr-D-Leu-Gly-L-(N-Cp)Phe-NH$_2$;
H-L-Tyr-D-Leu-Gly-L-(N-Al)Phe-NH$_2$; H-L-Tyr-D-Ile-Gly-L-(N-Al)Phe-NH$_2$;
H-L-Tyr-D-Ile-Gly-L-(N-Cp)Phe-NH$_2$;
H-L-Tyr-D-Thr-Gly-L-(N-Cp)Phe-NH$_2$;
H-L-Tyr-D-Thr-Gly-L-(N-Al)Phe-NH$_2$;
H-L-Tyr-D-Gly(Al)-Gly-L-(N-Cp)Phe-NH$_2$;
H-L-Tyr-D-Gly(Cp)-Gly-L-(N-Al)Phe-NH$_2$;
H-L-Tyr-D-Met-Gly-L-(N-Al)Phe-NH$_2$;
H-L-Tyr-D-Cys(Me)-Gly-L-(N-Cp)Phe-NH$_2$;
H-L-Tyr-D-Met(O)-Gly-L-(N-Cp)Phe-NH$_2$;
H-L-Tyr-D-Cys(Me)(O)-Gly-L-(N-Al)Phe-NH$_2$;
H-L-Tyr-D-Ser-Gly-L-(N-Al)Phe-NH$_2$;
H-L-Tyr-D-Ser-Gly-L-(N-Cp)Phe-NH$_2$;
(N-Me)-L-Tyr-D-Ala-Gly-L-(N-Al)Phe-NH$_2$;
(N-Me)-L-Tyr-D-Thr-Gly-L-(N-Al)Phe-NH$_2$;
H-L-Tyr-D-Hse-Gly-L-(N-Cp)Phe-NH$_2$;
(N-Me)-L-Tyr-D-Ala-Gly-L-(N-Cp)Phe-NH$_2$;
(N-Et)-L-Tyr-D-Abu-Gly-L-(N-Al)Phe-NH$_2$;
(N-Me)-L-Tyr-D-Val-Gly-L-(N-Cp)Phe-NH$_2$;
(N-Pr)-L-Tyr-D-Leu-Gly-L-(N-Al)Phe-NH$_2$;
(N-Me)-L-Tyr-D-Leu-Gly-L-(N-Al)Phe-NH$_2$;
(N-Me)-L-Tyr-D-Nva-Gly-L-(N-Cp)Phe-NH$_2$;
(N-Et)-L-Tyr-D-Ala-Gly-L-(N-Al)Phe-NH$_2$;
(N-Pr)-L-Tyr-D-Ala-Gly-L-(N-Al)Phe-NH$_2$;
(N-Et)-L-Tyr-D-Ala-Gly-L-(N-Cp)Phe-NH$_2$;
(N-Pr)-L-Tyr-D-Val-Gly-L-(N-Al)Phe-NH$_2$;
(N-Pr)-L-Tyr-D-Ala-Gly-L-(N-Cp)Phe-NH$_2$;
H-L-Tyr-D-Ala-Gly-L-(N-Cp)Phe-CH$_2$OH;
H-L-Tyr-D-Ala-Gly-L-(N-Al)Phe-CH$_2$OH;
H-L-Tyr-D-Abu-Gly-L-(N-Cp)Phe-CH$_2$OH;
H-L-Tyr-D-Abu-Gly-L-(N-Al)Phe-CH$_2$OH;
H-L-Tyr-D-Nva-Gly-L-(N-Cp)Phe-CH$_2$OH;
H-L-Tyr-D-Nva-Gly-L-(N-Al)Phe-CH$_2$OH;
H-L-Tyr-D-Val-Gly-L-(N-Cp)Phe-CH$_2$OH;
H-L-Tyr-D-Val-Gly-L-(N-Al)Phe-CH$_2$OH;
H-L-Tyr-D-Nle-Gly-L-(N-Cp)Phe-CH$_2$OH;
H-L-Tyr-D-Nle-Gly-L-(N-Al)Phe-CH$_2$OH;
H-L-Tyr-D-Leu-Gly-L-(N-Cp)Phe-CH$_2$OH;
H-L-Tyr-D-Leu-Gly-L-(N-Al)Phe-CH$_2$OH;
H-L-Tyr-D-Ile-Gly-L-(N-Al)Phe-CH$_2$OH;
H-L-Tyr-D-Ile-Gly-L-(N-Cp)Phe-CH$_2$OH;
H-L-Tyr-D-Thr-Gly-L-(N-Cp)Phe-CH$_2$OH;
H-L-Tyr-D-Thr-Gly-L-(N-Al)Phe-CH$_2$OH;
H-L-Tyr-D-Gly(Al)-Gly-L-(N-Al)Phe-CH$_2$OH;
H-L-Tyr-D-Gly(Cp)-Gly-L-(N-Cp)Phe-CH$_2$OH;
H-L-Tyr-D-Met-Gly-L-(N-Al)Phe-CH$_2$OH;
H-L-Tyr-D-Cys(Me)-Gly-L-(N-Al)Phe-CH$_2$OH;
H-L-Tyr-D-Met(O)-Gly-L-(N-Cp)Phe-CH$_2$OH;
H-L-Tyr-D-Cys(Me)(O)-Gly-L-(N-Al)Phe-CH$_2$OH;
H-L-Tyr-D-Ser-Gly-L-(N-Cp)Phe-CH$_2$OH;
H-L-Tyr-D-Ser-Gly-L-(N-Al)Phe-CH$_2$OH;
H-L-Tyr-D-Hse-Gly-L-(N-Al)Phe-CH$_2$OH;
(N-Me)-L-Tyr-D-Ala-Gly-L-(N-Cp)Phe-CH$_2$OH;
(N-Me)-L-Tyr-D-Ala-Gly-L-(N-Al)Phe-CH$_2$OH;
(N-Me)-L-Tyr-D-Thr-Gly-L-(N-Al)Phe-CH$_2$OH; (N-Et)-L-Tyr-D-Abu-Gly-L-(N-Cp)Phe-CH$_2$OH;
(N-Me)-L-Tyr-D-Val-Gly-L-(N-Al)Phe-CH$_2$OH;
(N-Pr)-L-Tyr-D-Leu-Gly-L-(N-Al)Phe-CH$_2$OH;
(N-Me)-L-Tyr-D-Leu-Gly-L-(N-Al)Phe-CH$_2$OH;
(N-Me)-L-Tyr-D-Nva-Gly-L-(N-Cp)Phe-CH$_2$OH;
(N-Et)-L-Tyr-D-Ala-Gly-L-(N-Al)Phe-CH$_2$OH;
(N-Et)-L-Tyr-D-Ala-Gly-L-(N-Cp)Phe-CH$_2$OH;
(N-Pr)-L-Tyr-D-Ala-Gly-L-(N-Al)Phe-CH$_2$OH;
(N-Pr)-L-Tyr-D-Ala-Gly-L-(N-Cp)Phe-CH$_2$OH;
(N-Pr)-L-Tyr-D-Leu-Gly-L-(N-Al)Phe-CH$_2$OH;
(N-Pr)-L-Tyr-D-Ala-Gly-L-(N-Al)Phe-CH$_2$OH;
H-L-Tyr-D-Ala-Gly-L-(N-Al)Phe-CH$_2$OAc;
H-L-Tyr-D-Ala-Gly-L-(N-Cp)Phe-CH$_2$OAcOMe;
H-L-Tyr-D-Ala-Gly-L-(N-Al)Phe-CH$_2$OAcOMe;
H-L-Tyr-D-Ala-Gly-L-(N-Cp)Phe-CH$_2$OAc;
(N-Me)-L-Tyr-D-Ala-Gly-L-(N-Al)Phe-CH$_2$OAcOMe;
(N-Me)-L-Tyr-D-Ala-Gly-L-(N-Cp)Phe-CH$_2$OAcOMe;
(N-Me)-L-Tyr-D-Ala-Gly-L-(N-Al)Phe-CH$_2$OAc;
(N-Me)-L-Tyr-D-Ala-Gly-L-(N-Cp)Phe-CH$_2$OAc;
(N-Et)-L-Tyr-D-Ala-Gly-L-(N-Al)Phe-CH$_2$OAc;
H-L-Tyr-D-Ala-Gly-L-(N-Al)Phe-OMe;
H-L-Tyr-D-Ala-Gly-L-(N-Cp)Phe-OEt;
H-L-Tyr-D-Abu-Gly-L-(N-Cp)Phe-OMe;
H-L-Tyr-D-Abu-Gly-L-(N-Al)Phe-Ome;
H-L-Tyr-D-Nva-Gly-L-(N-Cp)Phe-OPr;
H-L-Tyr-D-Nva-Gly-L-(N-Al)Phe-OIp;
H-L-Tyr-D-Val-Gly-L-(N-Cp)Phe-OMe;
H-L-Tyr-D-Val-Gly-L-(N-Al)Phe-OEt;
H-L-Tyr-D-Nle-Gly-L-(N-Cp)Phe-OEt;
H-L-Tyr-D-Nle-Gly-L-(N-Al)Phe-OMe;
H-L-Tyr-D-Leu-Gly-L-(N-Cp)Phe-OEt;
H-L-Tyr-D-Leu-Gly-L-(N-Al)Phe-OPr;
H-L-Tyr-D-Ile-Gly-L-(N-Cp)Phe-OMe;
H-L-Tyr-D-Ile-Gly-L-(N-Al)Phe-OMe;
H-L-Tyr-D-Ala-Gly-L-(N-Cp)Phe-OMe;
H-L-Tyr-D-Ala-Gly-L-(N-Al)Phe-OEt;
H-L-Tyr-D-Ala-Gly-L-(N-Al)Phe-OIp;
H-L-Tyr-D-Ala-Gly-L-(N-Al)Phe-OPr;
(N-Me)-L-Tyr-D-Ala-Gly-L-(N-Al)Phe-OMe;
(N-Me)-L-Tyr-D-Ala-Gly-L-(N-Cp)Phe-OMe;
(N-Me)-L-Tyr-D-Ala-Gly-L-(N-Al)Phe-OIp;
(N-Et)-L-Tyr-D-Ala-Gly-L-(N-Al)Phe-OMe;
(N-Me)-L-Tyr-D-Ala-Gly-L-(N-Al)Phe-OPr;
(N-Me)-L-Tyr-D-Ala-Gly-L-(N-Al)Phe-OEt;
H-L-Tyr-D-Gly(Al)-Gly-L-(N-Cp)Phe-OEt;
H-L-Tyr-D-Gly(Cp)-Gly-L-(N-Al)Phe-OPr;
H-L-Tyr-D-Met-Gly-L-(N-Cp)Phe-OMe;
H-L-Tyr-D-Cys(Me)-Gly-L-(N-Al)Phe-OPr;
H-L-Tyr-D-Met(O)-Gly-L-(N-Al)Phe-OIp;
H-L-Tyr-D-Cys(Me)(O)-Gly-L-(N-Cp)Phe-OMe;
H-L-Tyr-D-Ser-Gly-L-(N-Al)Phe-OEt;
(N-Pr)-L-Tyr-D-Ala-Gly-L-(N-Al)Phe-OEt;
H-L-Tyr-D-Thr-Gly-L-(N-Cp)Phe-OEt;
H-L-Tyr-D-Thr-Gly-L-(N-Al)Phe-OMe;
H-L-Tyr-D-Hse-Gly-L-(N-Al)Phe-OMe;
(N-Me)-L-Tyr-D-Thr-Gly-L-(N-Al)Phe-OMe;

(N-Et)-L-Tyr-D-Thr-Gly-L-(N-Al)Phe-OMe;
(N-Et)-L-Tyr-D-Ala-Gly-L-(N-Al)Phe-OMe;
(N-Et)-L-Tyr-D-Abu-Gly-L-(N-Cp)Phe-OEt;
(N-Me)-L-Tyr-D-Val-Gly-L-(N-Al)Phe-OMe;
(N-Pr)-L-Tyr-D-Leu-Gly-L-(N-Al)Phe-OMe;
(N-Me)-L-Tyr-D-Nle-Gly-L-(N-Al)Phe-OEt;
(N-Me)-L-Tyr-D-Ile-Gly-L-(N-Cp)Phe-OPr;
(N-Me)-L-Tyr-D-Leu-Gly-L-(N-Al)Phe-OIp;
(N-Me)-L-Tyr-D-Nva-Gly-L-(N-Cp)Phe-OIp;
(N-Me)-L-Tyr-D-Met-Gly-(N-Al)Phe-OPr;
H-L-Tyr-D-Ser-Gly-L-(N-Cp)Phe-OMe;
(N-Me)-L-Tyr-D-Met-Gly-L-(N-Al)Phe-OMe;
(N-Me)-L-Tyr-D-Val-Gly-L-(N-Cp)Phe-OMe;
H-L-Tyr-D-Gly(Al)-Gly-L-(N-Al)Phe-OMe;
(N-Me)-L-Tyr-D-Gly(Cp)-Gly-L-(N-Cp)Phe-OMe;
and the like.

The compounds of this invention are prepared by routine methods for peptide synthesis. It is possible, during the synthesis of certain of the compounds of this invention, that partial racemization can occur. However, the extent of racemization, should such occur, is not sufficient to significantly alter the analgesic activity of the compounds of this invention.

The compounds of this invention can be synthesized by solid phase peptide synthesis or by classical solution phase synthesis. In the solid phase method, the peptide chain is sequentially constructed using a resin support, typically a benzhydrylamine resin or a chloromethylated polystyrene resin. The product is cleaved from the resin with HF and purified, generally chromatographically.

Whichever method is used, the preparation of the compounds of this invention involves the coupling of amino acids or peptide fragments by reaction of the carboxyl function of one with the amino function of another to produce an amide linkage. In order to effectively achieve coupling, it is desirable, first, that all reactive functionalities not participating directly in the reaction be inactivated by the use of appropriate blocking groups, and, secondly, that the carboxyl function which is to be coupled be appropriately activated to permit coupling to proceed. All of this involves a careful selection of both reaction sequence and reaction conditions as well as utilization of specific blocking groups so that the desired peptide product will be realized. Each of the amino acids which is employed to produce the compounds of this invention and which has the particularly selected protecting groups and/or activating functionalities is prepared by techniques well recognized in the peptide art.

Selected combinations of blocking groups are employed at each point of the total synthesis of the compounds of this invention. These particular combinations have been found to function most smoothly. Other combinations would operate in the synthesis of the compounds of this invention, although, perhaps, with a lesser degree of success. Thus, for example, benzyloxycarbonyl, t-butyloxycarbonyl, t-amyloxycarbonyl, p-methoxybenzyloxycarbonyl, adamantyloxycarbonyl, and isobornyloxycarbonyl can be variously employed as amino blocking groups in the synthesis of the compounds of this invention. Furthermore, benzyl (Bzl) generally is employed as the hydroxy-protecting group for the tyrosyl residue even though others, such as p-nitrobenzyl (PNB), p-methoxybenzyl (PMB), and the like, could well be employed.

The carboxyl blocking groups used in preparing the compounds of this invention can be any of the typical ester-forming groups, including, for example, methyl, ethyl, benzyl, p-nitrobenzyl, p-methoxybenzyl, 2,2,2-trichloroethyl, and the like.

Coupling of the suitably protected N-blocked amino acid or peptide fragment with a suitably protected carboxy-blocked amino acid or peptide fragment in preparation of the compounds of this invention consists of rendering the free carboxyl function of the amino acid or peptide fragment active to the coupling reaction. This can be accomplished using any of several well recognized techniques. One such activation technique involves conversion of the carboxyl function to a mixed anhydride. The free carboxyl function is activated by reaction with another acid, typically a derivative of carbonic acid, such as an acid chloride thereof. Examples of acid chlorides used to form mixed anhydrides are ethyl chloroformate, phenyl chloroformate, sec-butyl chloroformate, isobutyl chloroformate, pivaloyl chloride, and the like. Preferably, isobutyl chloroformate is employed.

Another method of activating the carboxyl function for the purpose of carrying out the coupling reaction is by conversion to its active ester derivative. Such active esters include, for example, a 2,4,5-trichlorophenyl ester, a pentachlorophenyl ester, a p-nitrophenyl ester, and the like. Another coupling method available for use is the well-recognized azide coupling method.

The preferred coupling method in preparation of the compounds of this invention involves the use of N,N'-dicyclohexylcarbodiimide (DCC) to activate the free carboxyl function thereby permitting coupling to proceed. This activation and coupling technique is carried out employing an equimolar quantity of DCC relative to the amino acid or peptide fragment and is carried out in the presence of an equimolar quantity of 1-hydroxybenzotriazole (HBT). The presence of HBT suppresses undesirable side reactions including the possibility of racemization.

Cleavage of selected blocking groups is necessary at particular points in the synthetic sequence employed in preparation of the compounds of this invention. A chemist of ordinary skill in the art of peptide synthesis can readily select from representative protecting groups those groups which are compatible in the sense that selective cleavage of the product can be accomplished permitting removal of one or more but less than all of the protecting groups present on the amino acid or peptide fragment. These techniques are well recognized in the peptide art. A fuller discussion of the techniques which are available for selective cleavage is provided in the literature in Schröder and Lübke, *The Peptides*, Volume I, Academic Press, New York, (1965), and especially in the Table provided at pages 72–75 thereof.

Cleavage of carboxyl protecting groups can be accomplished by alkaline saponification. Relatively strong alkaline conditions, typically using an alkali metal hydroxide, such as sodium hydroxide, potassium hydroxide, lithium hydroxide, and the like, are generally employed to deesterify the protected carboxyl. The reaction conditions under which saponification is accomplished are well recognized in the art. Many of the carboxyl blocking groups also can be removed by catalytic hydrogenolysis including, for example, hydrogenolysis in the presence of a catalyst such as palladium on carbon. Furthermore, in those instances in which the carboxyl blocking group is p-nitrobenzyl or 2,2,2-trichloroethyl, deblocking can be accomplished by reduction in the presence of zinc and hydrochloric acid.

Many of the amino blocking groups are cleaved by treating the protected amino acid or peptide with an acid such as formic acid, trifluoroacetic acid (TFA), p-toluenesulfonic acid (TSA), benzenesulfonic acid (BSA), naphthalenesulfonic acid, and the like, to form the respective acid addition salt product. Cleavage of others, for example, benzyloxycarbonyl, can be accomplished by treating the blocked amino acid or peptide with a mixture of HBr and acetic acid to produce the corresponding hydrobromide acid addition salt. The particular method or reagent which is employed will depend upon the chemical or physical characteristics of the materials involved in the specific deblocking reaction. The resulting acid addition salt can be converted to a more pharmaceutically acceptable form by treatment with a suitable ion exchange resin, such as DEAE Sephadex A25, Amberlyst A27, and the like.

The hydroxy-protecting group can be retained on the peptide throughout the sequence of its preparation, being removed during the final synthetic step in conjunction with cleavage of the amino blocking group. However, depending upon the conditions employed for removal of the carboxyl blocking group, it may be removed earlier in the preparative sequence. When the carboxyl group is cleaved by alkaline saponification, the hydroxy-protecting group is retained; however, when catalytic hydrogenolysis is employed for removal of the carboxyl protecting group, the hydroxy protecting group also is cleaved. The latter situation does not represent a serious problem since preparation of the compounds of this invention can be accomplished in the presence of a tyrosyl residue having a free hydroxyl group, for example, a tyrosyl residue.

A preferred specific method for preparing compounds of this invention involves coupling a separately prepared dipeptide representing the second and third amino acid residues with a separately prepared C-terminal amino acid and coupling the resulting tripeptide to the N-terminal tyrosine. The separately prepared C-terminal amino acid can be structured so as to contain the amide, alcohol, ether, or ester moiety. Alternatively, it can contain a group which represents a precursor to the desired C-terminal moiety. The general sequence, illustrating preparation of a tetrapeptide of this invention, can be depicted as follows. In the sequence, the letter Z represents the C-terminal moiety, whether in its final form or as a precursor, the symbol AA represents an amino acid residue, and the number appended to the symbol AA represents the position of the amino acid in the ultimate peptide product sequence.

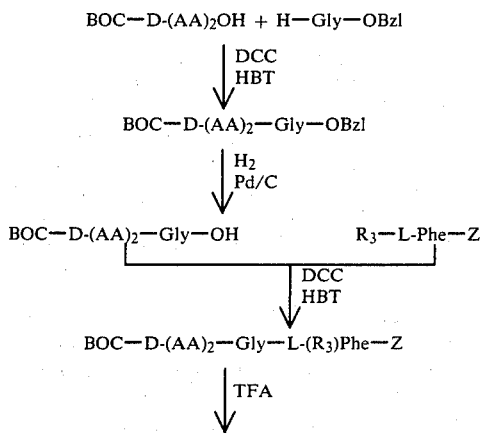

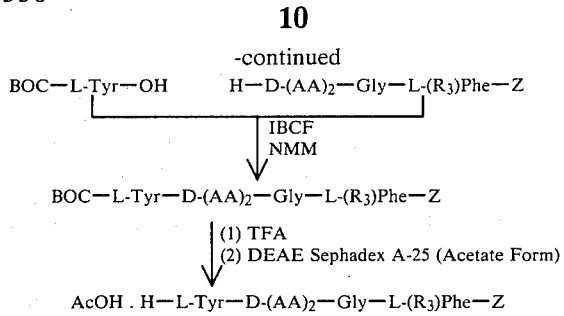

The above represents only one sequence for preparing compounds of this invention. Other sequences are available. Another solution method which can be employed involves the step-wise, sequential addition of single amino acids in construction of the peptide chain beginning with the C-terminal amino acid moiety. Reaction techniques such as those described above are employed in this as well as any other contemplated preparative sequence.

In the compounds of this invention, one or more of the groups $R_1$ and $R_3$ are, variously, alkyl, allyl, or cyclopropylmethyl. In these instances, the appropriate N-substituted amino acid is employed in the preparative sequence. One method for preparing the N-monosubstituted amino acids is as follows using an N-protected amino acid as starting material:

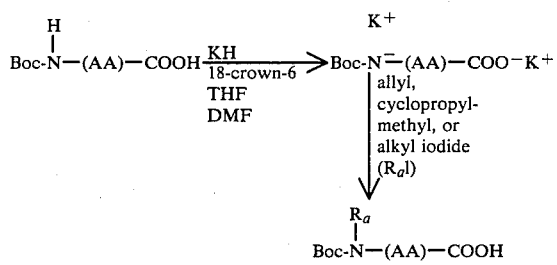

As the above sequence indicates, the amino acid first is treated with potassium hydride in the presence of a suitable crown ether to generate the dianion. The intermediate then is treated with the appropriate allyl, cyclopropylmethyl, or alkyl iodide to obtain the desired N-substituted amino acid. Another method for preparing the N-monosubstituted amino acid involves treating the N-unsubstituted amino acid in the form of its amide with about four equivalents of sodium bicarbonate and the appropriate allyl, cyclopropylmethyl, or alkyl halide in refluxing ethanol.

It will be apparent to those of ordinary skill in the art of peptide synthesis that racemization at the α-carbon can occur under strongly alkaline conditions such as those employed in the above alkylation procedure. The degree of racemization may vary depending upon the particular amino acid which is involved. Racemization can be minimized by using excess alkylating agent and by keeping the reaction time as short as possible. Nevertheless, even in the event that excessive racemization does occur, the product can be purified by recrystallization as the salt of d(+) α-phenylethylamine.

The C-terminal portion of the peptides of this invention is derivatized to its primary amide, ester, alcohol, or ether. Derivatization to the amide is accomplished by activation of the carboxyl group of the amino acid with N,N'-dicyclohexylcarbodiimide (DCC) in the presence of 1-hydroxybenzotriazole (HBT) to give the HBT ester. The ester then is reacted with anhydrous ammonia to give the amide.

The C-terminal esters are available from the corresponding acids by techniques well recognized in the art. Derivatization to the primary alcohol is achieved by preparing the methyl ester of the C-terminal amino acid or peptide. The ester then is reduced using sodium borohydride and lithium chloride to give the corresponding primary alcohol derivative.

The ethers can be prepared by any of a variety of well-recognized methods. One involves treating the corresponding alcohol in an aqueous sodium hydroxide medium with an alkyl bromide in which the alkyl group corresponds to the intended alkyl portion of the ether product.

The compounds of this invention are valuable pharmaceutical agents. They exhibit analgesic activity and also neuroleptic activity. They are especially useful in alleviation of pain and amelioration of emotional disturbances when administered parenterally or orally to mammals, including humans.

The compounds of this invention may be administered alone or in combination with pharmaceutically acceptable carriers, the proportion of which is determined by the solubility and chemical nature of the compound, the selected route of administration, and standard pharmaceutical practice.

Preferred compositions are those suitable for parenteral administration, that is, intramuscular, subcutaneous, or intravenous. These include sterile, injectable solutions or suspensions, and sterile injectable depot or slow-release formulations. Particularly convenient sterile, injectable solutions are made up in isotonic saline or isotonic dextrose. The sterile, injectable compositions can be prepared and stored as such or they can be prepared immediately prior to use by adding a sterile medium, for example, water, to a known weight of sterile ingredient enclosed in a vehicle, for example, a vial or an ampoule, which maintains sterility of the ingredient. The known weight of sterile ingredient may also contain sufficient sterile dextrose or sodium chloride to provide an isotonic solution or suspension after addition of the sterile medium.

Preferred compositions also are those suitable for oral administration. These can be prepared as discrete units such as capsules, tablets, and the like, each containing a predetermined amount of the active ingredient. Moreover, they, for example, can be prepared in powder or granule form, as a solution or a suspension in an aqueous or a non-aqueous medium, or as an emulsion.

The tablet can be prepared by compression, generally with one or more accessory ingredients. The tablets are prepared by compressing the active ingredient in a free-flowing form, such as a powder or granule, and generally mixed with one or more other ingredients, such as binders, lubricants, inert diluents, lubricating agents, surface active agents, buffers, flavoring agents, thickeners, preservatives, dispensing agents, and the like.

Physicians will determine the particular dosage of the compounds of this invention which is most suitable. The selected dosages will vary depending upon the mode of administration, the particular compound administered, the patient under treatment, and the kind of treatment. In general, however, the dosage will range from about 0.5 $\mu$g. to about 2 mg. per kilogram body weight of the recipient, and, preferably, from about 10 $\mu$g. to about 100 $\mu$g. per kilogram body weight, when administered intramuscularly or subcutaneously, and from about 0.1 $\mu$g. to about 500 $\mu$g. per kilogram body weight of the recipient, and, preferably, from about 5 $\mu$g, to about 50 $\mu$g, per kilogram body weight, when administered intravenously. When administered orally, the dosage generally will range from about 100 $\mu$g. to about 200 mg. per kilogram body weight of the recipient, and, preferably, from about 500 $\mu$g. to about 100 mg. per kilogram body weight, and, more preferably, from about 5 mg. to about 20 mg. per kilogram body weight.

The following examples are provided to illustrate the preparation and activity of the compounds of this invention. They are not intended to be limiting upon the scope thereof.

EXAMPLE 1

Preparation of
L-Tyrosyl-D-alanyl-glycyl-L-($N^\alpha$-allyl)phenylalanine Amide, Acetate Salt.

A. $N^\alpha$-t-Butyloxycarbonyl-$N^\alpha$-allyl-L-phenylalanine.

To 100 ml. of THF were added 10.6 grams (15 mmoles) of $N^\alpha$-t-butyloxycarbonyl-L-phenylalanine. The mixture was added dropwise over a one hour period to a mechanically stirred suspension of 0.12 moles of potassium hydride in 250 ml. of dried THF containing 0.5 grams of 18-crown-6-ether at 0° C. and under a nitrogen atmosphere. The mixture was stirred for an additional 10 minutes at 0° C., and a solution of 4 ml. (44 mmoles) of allyl iodide in 20 ml. of THF was added dropwise over a 30 minute period. The resulting mixture was maintained for four hours after which a mixture of 4.6 ml. of glacial acetic acid in 20 ml. of THF was added dropwise. The mixture was stirred for 10 minutes and then was poured onto 400 ml. of ice. The aqueous phase was adjusted to pH 8.0 by addition of 1 N sodium hydroxide. The aqueous phase then was extracted with ether and acidified to pH 2.0 with cold 1 N HCl. The aqueous mixture then was extracted with ethyl acetate. The ethyl acetate was extracted with water, dried over magnesium sulfate, and evaporated in vacuo to a syrup. The syrup was dissolved in 200 ml. of ether, and 8 ml. (0.04 moles) of dicyclohexylamine (DCHA) were added. The resulting precipitate was filtered, and the filtrate was extracted successively with 1.5 N citric acid and water. The ether layer was dried over magnesium sulfate and evaporated in vacuo to obtain 9 grams (74%) of the title compound as a syrup. $[\alpha]_D^{25} - 130.8°$ (c=0.5, MeOH).

NMR $\delta$1.25 ($H_2C=$); 1.45 (t-butyl); 7.25 (phenyl); and 10.5 (carboxyl).

B. $N^\alpha$-t-Butyloxycarbonyl-$N^\alpha$-allyl-L-phenylalanine Amide

The product from Part A (9 grams; 29.5 mmoles) was dissolved in 60 ml. of DMF. The mixture was cooled to 0° C., and 4.49 grams (29.5 mmoles) of HBT:ammonia complex and 6.08 grams (29.5 mmoles) of DCC were added to the mixture. The mixture was stirred for 2 hours at 0° C. and then for 72 hours at room temperature. The mixture then was cooled to 0° C. and filtered. The filtrate was concentrated in vacuo to an oil, and the oil was dissolved in ethyl acetate and extracted successively with 1 N sodium bicarbonate, water, cold 1.5 N citric acid, and water. The organic phase was dried over magnesium sulfate and concentrated in vacuo to an oil. The oil was mounted on a 3×40 cm. column of Grace and Davison grade 62 silica gel in chloroform. The product was eluted with a gradient of chloroform containing up to 5 percent methanol. The product was isolated according to a thin-layer profile of the fractions collected to give 3.55 grams (70 percent) of the title compound.

$[\alpha]_D^{25} - 114.7°$ (c=0.5, MeOH).

Analysis, Calculated for $C_{17}H_{24}N_2O_3$ (304.4): C, 67.08; H, 7.95; N, 9.20. Found: C, 67.34; H, 7.66; N, 8.98.

NMR $\delta 1.4$ (t-butyl); 7.2 (phenyl).

C. $N^\alpha$-Allyl-L-phenylalanine Amide, Hydrochloride Salt

To 50 ml. of fresh 1 N HCl (gas) in glacial acetic acid containing 5 ml. of anisole and 5 ml. of triethylsilane were added 5.9 grams (19.3 mmoles) of the product from Part B. The mixture was stirred at room temperature for 30 minutes and then was poured into ether. The resulting precipitate was collected and dried to give 4.1 grams (88 percent) of the title compound, m.p. 250°–253° C.

$[\alpha]_D^{25} + 12.1°$ (c=0.5, DMF).

Analysis, Calculated for $C_{12}H_{17}N_2OCl$ (240.7): C, 59.87; H, 7.12; N, 11.64. Found: C, 59.65; H, 6.84; N, 11.83.

NMR $\delta 3.45$ ($C_6H_5CH_2$—); 4.0 (—CH—); and 7.3 (phenyl).

D. $N^\alpha$-t-Butyloxycarbonyl-D-alanyl-glycyl-L-($N^\alpha$-allyl)-phenylalanine Amide To 20 ml. of DMF were added 1.2 grams (5 mmoles) of the product from Part C. The mixture was cooled to 0° C., and 2.19 grams (5 mmoles) of $N^\alpha$-t-butyloxycarbonyl-D-alanyl-glycine, dicyclohexylammonium salt were added. The mixture was stirred at 0° C. for five minutes, and 0.68 grams (5 mmoles) of HBT and 1.03 grams (5 mmoles) of DCC were added. The mixture was stirred at 0° C. for two hours and then at room temperature for 24 hours. The mixture then was cooled to 0° C., and the resulting precipitate was removed by filtration, and the filtrate was evaporated in vacuo. The resulting residue was dissolved in ethyl acetate, and the ethyl acetate was extracted successively with 1 N sodium bicarbonate, water, 0.75 N citric acid, and water. The organic phase was dried over magnesium sulfate and evaporated in vacuo to an oil. The oil was dissolved in acetone and placed on two preparative thin-layer plates. The plates were eluted with a 9:1 mixture of chloroform and methanol. The major component was cut from the TLC plates, and the title compound was eluted from the silica gel to give 1.1 grams (51 percent) of the title compound.

$[\alpha]_D^{25} - 64°$ (c=0.5, MeOH).

Analysis, Calculated for $C_{22}H_{32}N_4O_5$ (432.5): C, 61.09; H, 7.46; N, 12.95. Found: C, 60.89; H, 7.25; N, 12.66.

E. L-Tyrosyl-D-alanyl-glycyl-L-($N^\alpha$-allyl)phenylalanine Amide, Acetate Salt To 35 ml. of fresh 1 N HCl (gas) in glacial acetic acid containing 3 ml. of anisole and 3 ml. of triethylsilane were added 900 mg. (2.1 mmoles) of the product from Part D. The mixture was stirred at room temperature for 25 minutes and then was poured into ether. The resulting precipitate was collected and dried (700 mg.).

$N^{60}$-t-Butyloxycarbonyl-L-tyrosine (533 mg.; 1.9 mmoles) was suspended in 5 ml. of DMF. The mixture was cooled to −15° C., and 0.25 ml. (1.9 mmoles) of isobutyl chloroformate and 0.21 ml. (1.9 mmoles) of NMM were added rapidly to the stirred, cooled solution. Stirring of the solution at −15° C. was continued during preparation of the following.

The above hydrochloride (700 mg.; 1.9 mmoles) was dissolved in 5 ml. of DMF. The mixture was cooled to 0° C., and 0.21 ml. (1.9 mmoles) of NMM was added in one portion. The solution was agitated to ensure complete reaction. The resulting mixture was added rapidly to the above prepared solution, and the mixture was stirred for 2.5 hours at −15° C. The mixture then was poured onto a mixture of crushed ice and 1 N sodium bicarbonate. The aqueous solution then was extracted with ethyl acetate. The organic phase was separated and washed successively with water, 1.5 N citric acid, and water. The ethyl acetate then was dried over magnesium sulfate and concentrated in vacuo to an oil (1.0 gram).

The above oil (900 mg.) was dissolved in 15 ml. of trifluoroacetic acid containing 1.5 ml. of anisole and 1.5 of triethylsilane. The mixture was stirred at 0° C. for 30 minutes and poured into ether, and the resulting precipitate was collected and dried (700 mg.). The material was dissolved in sufficient buffer (1 percent pyridine; 0.05 percent acetic acid) to make 10 ml. of solution and the solution was applied to a 2.5×90 cm. column of Sephadex DEAE A-25 (acetate) previously equilibrated with the same buffer. The eluate was monitored at 280 nm, and the appropriate fractions were combined and lyophilized to give a white solid. The solid was dissolved in 10 ml. of 0.2 M acetic acid, and the solution was applied to a 2.5×90 cm. Sephadex G-10 column. The column was eluted with 0.2 M acetic acid, and the eluate was monitored at 280 nm. The appropriate fractions were combined and lyophilized to give 463 mg. (40 percent) of the title compound as a white solid.

$[\alpha]_D^{25} - 1.19°$ (c=0.5, 1 N HCl).

Analysis, Calculated for $C_{28}H_{37}N_5O_7$ (555.6): C, 60.53; H, 6.71; N, 12.60. Found: C, 60.26; H, 6.67; N, 12.89.

Amino Acid Analysis: Tyr, 1.00; Ala, 0.99; Gly, 1.00; $NH_3$, 0.98.

EXAMPLE 2

Preparation of L-Tyrosyl-D-alanyl-glycyl-L-($N^\alpha$-cyclopropylmethyl)-phenylalanine Amide, Acetate Salt

A. $N^\alpha$-Cyclopropylmethyl-L-phenylalanine Amide

To 100 ml. of anhydrous ethyl alcohol were added 8 grams (0.04 mole) of L-phenylalanine amide hydrochloride. To the mixture then were added 13.4 grams (0.16 mole) of solid anhydrous sodium bicarbonate and 6.44 grams (0.048 mole) of bromomethylcyclopropane. The mixture was refluxed for seven hours and then was evaporated in vacuo to an oil. The oil was dissolved in ethyl acetate, and the ethyl acetate solution was extracted with water. The organic phase was dried over magnesium sulfate and evaporated in vacuo to an oil. The oil was applied to a 3×50 cm. column of Grace and Davison grade 62 silica gel in chloroform. The product was eluted with a gradient of chloroform containing up to 5 percent methanol. The product was isolated according to the thin-layer profile of the fractions collected to give 3.41 grams (39 percent) of the title compound.

NMR $\delta 1.45$ (H—N—); 7.3 (phenyl).

B.
N$^\alpha$-t-Butyloxycarbonyl-D-alanyl-glycyl-L-(N$^\alpha$-Cyclopropylmethyl)phenylalanine Amide The product from Part A (3.41 grams; 0.016 mole) was dissolved in 25 ml. of DMF. The mixture was cooled to 0° C., and 4.23 grams (0.016 mole) of N$^\alpha$-t-butyloxycarbonyl-D-alanyl-glycine were added followed by 2.16 grams (0.016 mole) of HBT and 3.03 grams (0.016 mole) of DCC. The mixture was stirred at 0° C. for two hours and then at room temperature for two days. The mixture then was cooled to 0° C., the resulting precipitate was removed by filtration, and the filtrate was evaporated in vacuo. The residue was dissolved in ethyl acetate, and the ethyl acetate was extracted successively with 1 N sodium bicarbonate, water, 1.5 N citric acid, and water. The organic phase then was dried over magnesium sulfate and evaporated in vacuo to a solid. The solid was applied to a 3×50 cm. column of Grace and Davison grade 62 silica gel in chloroform. The product was eluted with a gradient of chloroform containing up to five percent methanol. The product was isolated according to the thin-layer profile of the fractions collected to give 2.51 grams (35 percent) of the title compound, m.p. 83°-84° C.

Analysis, Calculated for $C_{23}H_{36}N_4O_5$ (448.6): C, 61.59; H, 8.09, N, 12.49. Found: C, 60.05; H, 7.40, N, 13.23.

C.
N$^\alpha$-t-Butyloxycarbonyl-L-tyrosyl-D-alanyl-glycyl-L-(N$^\alpha$-cyclopropylmethyl)phenylalanine Amide The product from Part B (2.4 grams; 5.3 mmoles) was dissolved in 20 ml. of trifluoroacetic acid containing 5 ml. of anisole. The mixture was stirred at 0° C. for 30 minutes after which the solvent was evaporated in vacuo without addition of heat. Ether was added to the resulting oil, the supernate was decanted, and the remaining oil was dried in vacuo.

To 10 ml. of DMF were added 1.4 grams (5.3 mmoles) of N$^\alpha$-t-butyloxycarbonyl-L-tyrosine. The mixture was cooled to −15° C., and 0.58 ml. (5.3 mmoles) of NMM and 0.69 ml. (5.3 mmoles) of isobutyl chloroformate were added rapidly to the stirred solution. The solution was stirred at −15° C. during which the following was prepared.

The trifluoroacetate salt from above was dissolved in 10 ml. of DMF. The mixture was cooled to −15° C., and 0.58 ml. of NMM was added in one portion. The mixture was agitated to ensure complete reaction and was added to the above mixed anhydride solution. The resulting mixture was stirred for four hours and then was poured onto a mixture of crushed ice and 1 N sodium bicarbonate. The aqueous solution was extracted with ethyl acetate, and the ethyl acetate then was extracted successively with water, 1.5 N citric acid, and water. The ethyl acetate was dried over magnesium sulfate and concentrated in vacuo to an oil (2.7 grams).

The oil was applied to four preparative thin-layer plates. The plates were eluted with a 9:1 mixture of chloroform and methanol. The major component was cut from the tlc plates, and the product was eluted from the silica gel to give 2.0 grams (62 percent) of the title compound.

$[\alpha]_D^{25} - 38.44°$ (c=0.5, MeOH).

Analysis, Calculated for $C_{32}H_{43}N_5O_7$ (609.7): C, 63.04; H, 7.11; N, 11.49. Found: C, 61.92; H, 6.89; N, 11.13.

Amino Acid Analysis: Tyr, 1.02; Ala, 0.99; Gly, 0.99; $NH_3$, 1.01.

D.
L-Tyrosyl-D-alanyl-glycyl-L-(N$^\alpha$-cyclopropylmethyl)-phenylalanine Amide, Acetate Salt The product from Part C (1.7 grams; 2.8 mmoles) was dissolved in 15 ml. of trifluoroacetic acid containing 3 ml. of anisole. The mixture was stirred at 0° C. for thirty minutes and then was freeze-dried. The resulting solid was dissolved in sufficient buffer (1 percent pyridine; 0.05 percent acetic acid) to make 10 ml., and the solution was applied to a 2.5×90 cm. column of Sephadex DEAE A-25 (acetate) which had been equilibrated with the same buffer. The eluate was monitored at 280 nm, and the appropriate fractions were combined and lyophilized. The resulting solid was dissolved in 10 ml. of 0.2 M acetic acid, and the solution was applied to a 2.5×90 cm. column of Sephadex G-10 equilibrated in the same solvent. The eluate was monitored at 280 nm, and the appropriate fractions were combined and lyophilized to give 1.3 grams (82 percent) of the title compound.

$[\alpha]_D^{25} - 20.2°$ (c=0.5, MeOH).

Analysis, Calculated for $C_{29}H_{39}N_5O_7$ (569.7): C, 61.15; H, 6.90; N, 12.29. Found: C, 61.38; H, 6.66; N, 12.06.

Amino Acid Analysis: Tyr, 1.00; Ala, 1.00; Gly, 0.99; $NH_3$, 1.02.

The analgesic activity of the compounds of this invention is demonstrated by the mouse hot plate test. In this test, a mouse is placed inside an upright acrylic cylinder comprising, as its base, a hot plate surface which is maintained at 52° C. The mouse is given, orally or by subcutaneous injection, a predetermined amount of test compound dissolved or suspended in a suitable carrier, and, 15 minutes after administration of the test compound, the mouse is placed on the hot plate surface. The latency in seconds until the mouse jumps from the hot plate surface is measure. An agent which exhibits analgesic activity produces an increase in this latency over that of control mice which receive only the carrier. This must occur in a dose range which produces no motor incoordination or incapacitation. The following Table records the ED$_{50}$ results obtained from this test.

TABLE

| Analgesic Activity, Hot Plate Test | |
|---|---|
| Compound | ED$_{50}$, mg./kg. subcutaneous |
| Example 1 | 0.01 |
| Example 2 | 0.012 |

We claim:

1. A compound of the formula

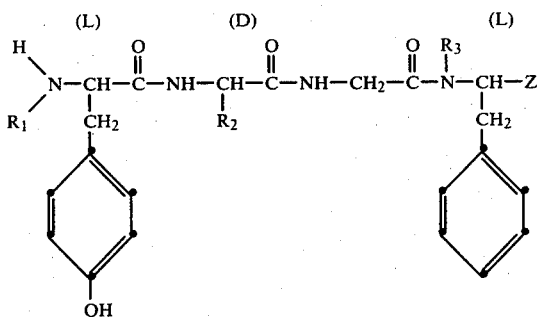

and pharmaceutically acceptable non-toxic acid addition salts thereof, in which L and D define the chirality;

$R_1$ is hydrogen or $C_1$–$C_3$ primary alkyl;

$R_2$ is $C_1$–$C_4$ primary or secondary alkyl, allyl, cyclopropylmethyl, $C_1$–$C_2$ hydroxyalkyl, or —(CH$_2$)$_m$—U—CH$_3$ in which U is —S— or >S—O and m is 1 or 2;

$R_3$ is cyclopropylmethyl; and

Z is —CH$_2$OR$_4$,

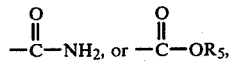

in which $R_4$ is hydrogen, acetyl, or acetoxymethyl and $R_5$ is $C_1$–$C_3$ alkyl.

2. Compound of claim 1, in which $R_3$ is cyclopropylmethyl.

3. Compound of claim 2, in which $R_1$ is hydrogen.

4. Compound of claim 3, in which Z is

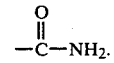

5. Compound of claim 4, in which $R_2$ is $C_1$–$C_4$ primary or secondary alkyl or $C_1$–$C_2$ hydroxyalkyl.

6. Compound of claim 5, in which $R_2$ is $C_1$–$C_4$ primary or secondary alkyl.

7. Compound of claim 6, in which $R_2$ is methyl.

8. Compound of claim 2, in which $R_1$ is $C_1$–$C_3$ primary alkyl.

9. Compound of claim 8, in which Z is

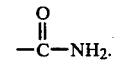

10. Compound of claim 9, in which $R_2$ is $C_1$–$C_4$ primary or secondary alkyl or $C_1$–$C_2$ hydroxyalkyl.

11. Compound of claim 10, in which $R_2$ is $C_1$–$C_4$ primary or secondary alkyl.

12. Compound of claim 11, in which $R_2$ is methyl.

13. Compound of claim 12, in which $R_1$ is methyl.

* * * * *